(12) United States Patent
Litherland et al.

(10) Patent No.: US 6,978,941 B2
(45) Date of Patent: *Dec. 27, 2005

(54) BASE ISOLATED NEBULIZING DEVICE AND METHODS

(75) Inventors: Craig M. Litherland, Cupertino, CA (US); Joseph Loeffler, Mountain View, CA (US); Joe Maxwell, Mountain View, CA (US)

(73) Assignee: Aerogen, Inc., Sunnyvale, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 10/821,444

(22) Filed: Apr. 9, 2004

(65) Prior Publication Data

US 2004/0188534 A1   Sep. 30, 2004

Related U.S. Application Data

(63) Continuation of application No. 09/848,104, filed on May 2, 2001, now Pat. No. 6,732,944.

(51) Int. Cl.[7] ............................. B05B 17/04; B05B 1/08
(52) U.S. Cl. .................... 239/4; 239/102.1; 239/102.2; 239/338; 239/548
(58) Field of Search ...................... 239/4, 102.1, 102.2, 239/338, 548, 552, 596

(56) References Cited

U.S. PATENT DOCUMENTS

| | | | |
|---|---|---|---|
| 550,315 A | 11/1895 | Allen | |
| 809,159 A | 1/1906 | Willis et al. | |
| 1,680,616 A | 8/1928 | Horst | |
| 2,022,520 A | 11/1935 | Philbrick | |
| 2,101,304 A | 12/1937 | Wright | |
| 2,158,615 A | 5/1939 | Wright | |
| 2,187,528 A | 1/1940 | Wing | |
| 2,223,541 A | 12/1940 | Baker | |
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |

(Continued)

FOREIGN PATENT DOCUMENTS

CH          477 855          9/1969

(Continued)

OTHER PUBLICATIONS

Abys, J.A. et al., "Annealing Behavior of Palladium-Nickel Alloy Electrodeposits," Plating and Surface Finishing, Aug. 1996, pp. 1-7.

(Continued)

*Primary Examiner*—Steven J. Ganey
(74) *Attorney, Agent, or Firm*—Townsend and Townsend and Crew LLP

(57) ABSTRACT

An aerosol generator comprises a vibratable member having a front, a rear, an outer periphery and a plurality of apertures extending between the front and the rear. A support element is disposed about the outer periphery of the vibratable member, and a vibratable element is coupled to the support element. The vibratable element is configured to vibrate the vibratable member at ultrasonic frequencies. An isolating structure is coupled to the support element and is configured to couple the aerosol generator to a support structure. The isolating structure has a mechanical vibrational impedance that is sufficient to substantially vibrationally isolate the aerosol generator from the support structure.

18 Claims, 5 Drawing Sheets

U.S. PATENT DOCUMENTS

| | | |
|---|---|---|
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singier |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,838,686 A | 10/1974 | Szekely |
| 3,842,833 A | 10/1974 | Ogle |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,030,492 A | 6/1977 | Simburner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rsenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |

| | | | | | | |
|---|---|---|---|---|---|---|
| 4,389,071 A | 6/1983 | Johnson, Jr. et al. | | 5,046,627 A | 9/1991 | Hansen |
| 4,408,719 A | 10/1983 | Last | | 5,062,419 A | 11/1991 | Rider |
| 4,428,802 A | 1/1984 | Kanai et al. | | 5,063,396 A | 11/1991 | Shiokawa et al. |
| 4,431,136 A | 2/1984 | Janner et al. | | 5,063,922 A | 11/1991 | Häkkinen |
| 4,454,877 A | 6/1984 | Miller et al. | | 5,073,484 A | 12/1991 | Swanson et al. |
| 4,465,234 A | 8/1984 | Maehara et al. | | 5,076,266 A | 12/1991 | Babaev |
| 4,474,251 A | 10/1984 | Johnson, Jr. | | 5,080,093 A | 1/1992 | Raabe et al. |
| 4,474,326 A | 10/1984 | Takahashi | | 5,080,649 A | 1/1992 | Vetter |
| 4,475,113 A | 10/1984 | Lee et al. | | 5,086,765 A | 2/1992 | Levine |
| 4,479,609 A | 10/1984 | Maeda et al. | | 5,086,785 A | 2/1992 | Gentile et al. |
| 4,512,341 A | 4/1985 | Lester | | 5,115,803 A | 5/1992 | Sioutas |
| 4,530,464 A | 7/1985 | Yamamoto et al. | | 5,115,971 A | 5/1992 | Greenspan et al. |
| 4,533,082 A | 8/1985 | Maehara et al. | | D327,008 S | 6/1992 | Friedman |
| 4,539,575 A | 9/1985 | Nilsson | | 5,122,116 A | 6/1992 | Kriesel et al. |
| 4,544,933 A | 10/1985 | Heinzl | | 5,129,579 A | 7/1992 | Conte |
| 4,546,361 A | 10/1985 | Brescia et al. | | 5,134,993 A | 8/1992 | Van Der Linden et al. |
| 4,550,325 A | 10/1985 | Viola | | 5,139,016 A | 8/1992 | Waser |
| 4,566,452 A | 1/1986 | Farr | | 5,140,740 A | 8/1992 | Weigelt |
| 4,591,883 A | 5/1986 | Isayama | | 5,147,073 A | 9/1992 | Cater |
| 4,593,291 A | 6/1986 | Howkins | | 5,152,456 A | 10/1992 | Ross et al. |
| 4,605,167 A | 8/1986 | Maehara | | 5,157,372 A | 10/1992 | Langford |
| 4,613,326 A | 9/1986 | Szwarc | | 5,164,740 A | 11/1992 | Ivri |
| 4,620,201 A | 10/1986 | Heinzl et al. | | 5,169,029 A | 12/1992 | Behar et al. |
| 4,628,890 A | 12/1986 | Freeman | | 5,170,782 A | 12/1992 | Kocinski |
| 4,632,311 A | 12/1986 | Nakane et al. | | 5,180,482 A | 1/1993 | Abys et al. |
| 4,658,269 A | 4/1987 | Rezanka | | 5,186,164 A | 2/1993 | Raghuprasad |
| 4,659,014 A | 4/1987 | Soth et al. | | 5,186,166 A | 2/1993 | Riggs et al. |
| 4,677,975 A | 7/1987 | Edgar et al. | | 5,198,157 A | 3/1993 | Bechet |
| 4,678,680 A | 7/1987 | Abowitz | | 5,201,322 A | 4/1993 | Henry et al. |
| 4,679,551 A | 7/1987 | Anthony | | 5,213,860 A | 5/1993 | Laing |
| 4,681,264 A | 7/1987 | Johnson, Jr. | | 5,217,148 A | 6/1993 | Cater |
| 4,693,853 A | 9/1987 | Falb et al. | | 5,217,492 A | 6/1993 | Guire et al. |
| 4,702,418 A | 10/1987 | Carter et al. | | 5,227,168 A | 7/1993 | Chvapil |
| 4,722,906 A | 2/1988 | Guire | | 5,230,496 A | 7/1993 | Shillington et al. |
| 4,753,579 A | 6/1988 | Murphy | | 5,245,995 A | 9/1993 | Sullivan et al. |
| 4,790,479 A | 12/1988 | Matsumoto et al. | | 5,248,087 A | 9/1993 | Dressler |
| 4,793,339 A | 12/1988 | Matsumoto et al. | | 5,258,041 A | 11/1993 | Guire et al. |
| 4,796,807 A | 1/1989 | Bendig et al. | | 5,261,601 A | 11/1993 | Ross et al. |
| 4,799,622 A | 1/1989 | Ishikawa et al. | | 5,263,992 A | 11/1993 | Guire |
| 4,805,609 A | 2/1989 | Roberts et al. | | 5,279,568 A | 1/1994 | Cater |
| 4,819,629 A | 4/1989 | Jonson | | 5,297,734 A | 3/1994 | Toda |
| 4,819,834 A | 4/1989 | Thiel | | 5,299,739 A | 4/1994 | Takahashi et al. |
| 4,826,080 A | 5/1989 | Ganser | | 5,303,854 A | 4/1994 | Cater |
| 4,826,759 A | 5/1989 | Guire et al. | | 5,309,135 A | 5/1994 | Langford |
| 4,828,886 A | 5/1989 | Hieber | | 5,312,281 A | 5/1994 | Takahashi et al. |
| 4,843,445 A | 6/1989 | Stemme | | 5,313,955 A | 5/1994 | Rodder |
| 4,849,303 A | 7/1989 | Graham et al. | | 5,319,971 A | 6/1994 | Osswald et al. |
| 4,850,534 A | 7/1989 | Takahashi et al. | | 5,320,603 A | 6/1994 | Vetter et al. |
| 4,865,006 A | 9/1989 | Nogi et al. | | 5,322,057 A | 6/1994 | Raabe et al. |
| 4,871,489 A | 10/1989 | Ketcham | | 5,342,011 A | 8/1994 | Short |
| 4,872,553 A | 10/1989 | Suzuki et al. | | 5,342,504 A | 8/1994 | Hirano et al. |
| 4,877,989 A | 10/1989 | Drews et al. | | 5,347,998 A | 9/1994 | Hodson et al. |
| 4,888,516 A | 12/1989 | Daeges et al. | | 5,348,189 A | 9/1994 | Cater |
| 4,922,901 A | 5/1990 | Brooks et al. | | 5,350,116 A | 9/1994 | Cater |
| 4,926,915 A | 5/1990 | Deussen et al. | | 5,355,872 A | 10/1994 | Riggs et al. |
| 4,934,358 A | 6/1990 | Nilsson et al. | | 5,357,946 A | 10/1994 | Kee et al. |
| 4,954,225 A | 9/1990 | Bakewell | | 5,372,126 A | 12/1994 | Blau |
| 4,957,239 A | 9/1990 | Tempelman | | 5,383,906 A | 1/1995 | Burchett et al. |
| 4,964,521 A | 10/1990 | Wieland et al. | | 5,388,571 A | 2/1995 | Roberts et al. |
| D312,209 S | 11/1990 | Morrow et al. | | 5,392,768 A | 2/1995 | Johansson et al. |
| 4,968,299 A | 11/1990 | Ahlstrand et al. | | 5,396,883 A | 3/1995 | Knupp et al. |
| 4,971,665 A | 11/1990 | Sexton | | 5,414,075 A | 5/1995 | Swan et al. |
| 4,973,493 A | 11/1990 | Guire | | 5,415,161 A | 5/1995 | Ryder |
| 4,976,259 A | 12/1990 | Higson et al. | | 5,419,315 A | 5/1995 | Rubsamen |
| 4,979,959 A | 12/1990 | Guire | | 5,426,458 A | 6/1995 | Wenzel et al. |
| 4,994,043 A | 2/1991 | Ysebaert | | 5,431,155 A | 7/1995 | Marelli |
| 5,002,048 A | 3/1991 | Makiej, Jr. | | 5,435,282 A | 7/1995 | Haber et al. |
| 5,002,582 A | 3/1991 | Guire et al. | | 5,435,297 A | 7/1995 | Klein |
| 5,007,419 A | 4/1991 | Weinstein et al. | | 5,437,267 A | 8/1995 | Weinstein et al. |
| 5,016,024 A | 5/1991 | Lam et al. | | 5,445,141 A | 8/1995 | Kee et al. |
| 5,021,701 A | 6/1991 | Takahashi et al. | | D362,390 S | 9/1995 | Weiler |
| 5,022,587 A | 6/1991 | Hochstein | | 5,449,502 A | 9/1995 | Igusa et al. |
| 5,024,733 A | 6/1991 | Abys et al. | | 5,452,711 A | 9/1995 | Gault |

| | | |
|---|---|---|
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,542,410 A | 8/1996 | Goodman et al. |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A | 12/1996 | Salter et al. |
| 5,586,550 A | 12/1996 | Ivri et al. |
| 5,588,166 A | 12/1996 | Burnett |
| 5,601,077 A | 2/1997 | Imbert |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |
| 5,657,926 A | 8/1997 | Toda |
| 5,660,166 A | 8/1997 | Lloyd |
| 5,664,557 A | 9/1997 | Makiej, Jr. |
| 5,664,706 A | 9/1997 | Cater |
| 5,665,068 A | 9/1997 | Takamura |
| 5,666,946 A | 9/1997 | Langenback |
| 5,670,999 A | 9/1997 | Takeuchi et al. |
| 5,685,491 A | 11/1997 | Marks et al. |
| 5,692,644 A | 12/1997 | Gueret |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |
| 5,790,151 A | 8/1998 | Mills |
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,007,518 A | 12/1999 | Kriesel et al. |
| 6,012,450 A | 1/2000 | Rubsamen |
| 6,014,970 A | 1/2000 | Ivri et al. |
| 6,026,809 A | 2/2000 | Abrams et al. |
| 6,032,665 A | 3/2000 | Psaros |
| 6,037,587 A | 3/2000 | Dowell et al. |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,270,473 B1 | 8/2001 | Schwebel |
| 6,273,342 B1 | 8/2001 | Terada et al. |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,615,824 B2 | 9/2003 | Power |

| | | | |
|---|---|---|---|
| 6,629,646 B1 | 10/2003 | Ivri | |
| 6,640,804 B2 | 11/2003 | Ivri | |
| 6,651,650 B1 | 11/2003 | Yamamoto et al. | |
| 6,732,944 B2 * | 5/2004 | Litherland et al. | 239/4 |
| 6,755,189 B2 | 6/2004 | Ivri et al. | |
| 6,769,626 B1 | 8/2004 | Haveri | |
| 6,782,886 B2 | 8/2004 | Narayan et al. | |
| 6,814,071 B2 | 11/2004 | Klimowicz et al. | |
| 6,845,770 B2 | 1/2005 | Klimowicz et al. | |
| 6,851,626 B2 | 2/2005 | Patel et al. | |
| 6,860,268 B2 | 3/2005 | Bohn et al. | |
| 2001/0013554 A1 | 8/2001 | Borland et al. | |
| 2001/0015737 A1 | 8/2001 | Truninger et al. | |
| 2002/0011247 A1 | 1/2002 | Ivri et al. | |
| 2002/0104530 A1 | 8/2002 | Ivri et al. | |
| 2002/0121274 A1 | 9/2002 | Borland et al. | |
| 2002/0134372 A1 | 9/2002 | Loeffler et al. | |
| 2002/0134374 A1 | 9/2002 | Loeffler et al. | |
| 2002/0134375 A1 | 9/2002 | Loeffler et al. | |
| 2002/0134377 A1 | 9/2002 | Loeffler et al. | |
| 2002/0162551 A1 | 11/2002 | Litherland | |
| 2003/0140921 A1 | 7/2003 | Smith et al. | |
| 2003/0150445 A1 | 8/2003 | Power et al. | |
| 2003/0150446 A1 | 8/2003 | Patel et al. | |
| 2003/0226906 A1 | 12/2003 | Ivri | |
| 2004/0000598 A1 | 1/2004 | Ivri | |
| 2004/0004133 A1 | 1/2004 | Ivri et al. | |
| 2004/0035490 A1 | 2/2004 | Power | |
| 2004/0050947 A1 | 3/2004 | Power et al. | |
| 2004/0139963 A1 | 7/2004 | Ivri et al. | |
| 2004/0139968 A1 | 7/2004 | Loeffler et al. | |
| 2004/0256488 A1 | 12/2004 | Loeffler et al. | |
| 2005/0011514 A1 | 1/2005 | Power et al. | |

FOREIGN PATENT DOCUMENTS

| | | |
|---|---|---|
| CH | 555 681 | 11/1974 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| FR | 2 692 569 | 12/1993 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| GB | 2 279 571 A | 1/1995 |
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 | 1/1994 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/010910 A1 | 6/1993 |
| WO | WO 94/09912 A1 | 5/1994 |
| WO | WO 96/09229 | 3/1996 |
| WO | WO 99/17888 | 4/1999 |
| WO | WO 00/37132 | 6/2000 |

OTHER PUBLICATIONS

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berglund, R.N., et al. "Generation of Monodisperse Aerosol Standards" Environ. Sci. Technology, Feb. 1973, pp. 147-153, vol. 7, No. 2.

Gaiser Tool Company catalog, pp. 26, 29-30 (1990).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkal Zenkoku Taikai Koenkai Koen Ronbunshu 69:660-662 (1991).

Palla Tech Pd an Pd Alloy Processes-Procedure for the Analysis of Additive IVS in Palla Tech Plating Solutions by HPLC, Technical Bulletin, Electroplating Chemicals & Services, 029-A, Lucent Technologies., pp. 1-5, 1996.

SIEMENS, "Servo Ultra Nebulizer 345 Operating Manual," pp. 1-23.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

Cipolla, D.C. et al., "Assessment of Aerosol Delivery Systems for Recombinant Human Deoxyribonuclease," S. T.P. Pharma Sciences 4 (1) 50-62, 1994.

Cipolla, D.C. et al., "Characterization of Aerosols of Human Recombinant Deoxyribonuclease I (rhDNase) Generated by Neulizers, " Pharmaceutical Research II (4) 491-498, 1994.

Gonda, I. "Therapeutic Aerosols," Pharmaceutics, The Science of Dosage Form Design, Editor: M.E. Aulton, 341-358, 1988.

\* cited by examiner

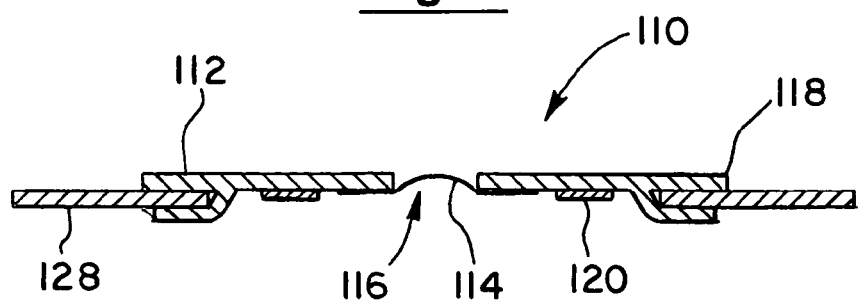
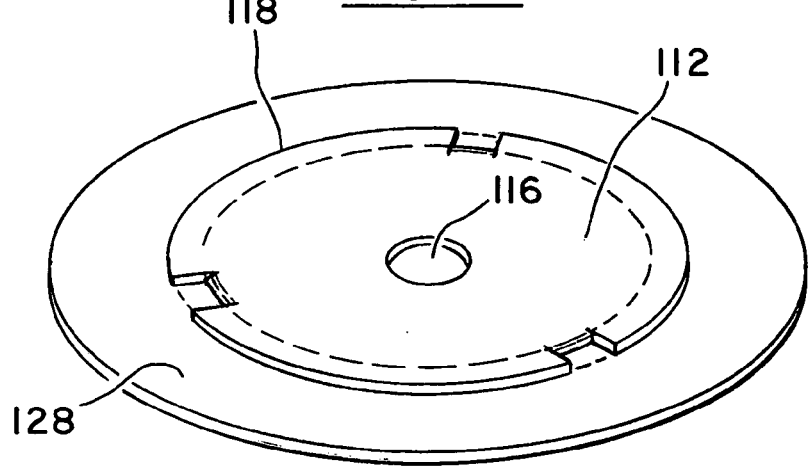
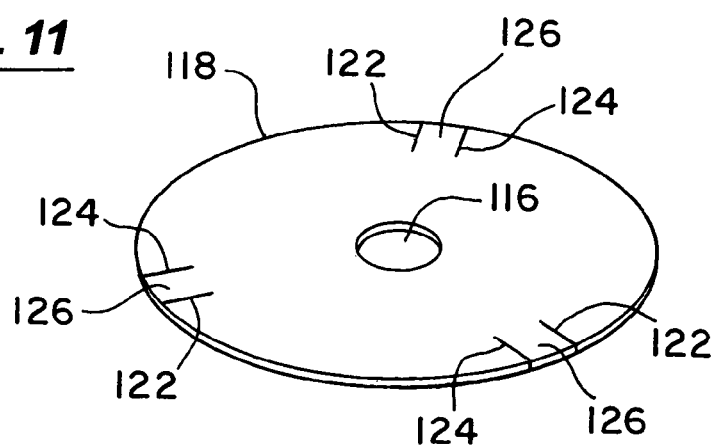

BASE ISOLATED NEBULIZING DEVICE AND METHODS

BACKGROUND OF THE INVENTION

This invention is related generally to the field of aerosolization of liquids, and in particular to the aerosolization of liquids using an aerosol generator that operates at ultrasonic vibrational frequencies. More specifically, the invention relates to techniques for vibrationally isolating an aerosol generator that is connected to another structure, such as the housing of an aerosolization device, when aerosolizing a liquid.

Aerosolization of liquids is an important aspect of many businesses. For example, liquids are commonly aerosolized in connection with drug delivery, air humidification, deodorant or insecticide delivery, and the like. One exemplary way to aerosolize liquids is by supplying liquid to a vibratable member having a plurality of apertures and vibrating the vibratable member at ultrasonic frequencies. One way to vibrate the vibratable member is by use of a piezoelectric transducer. Such techniques are described in, for example, U.S. Pat. Nos. 5,164,740; 5,938,117; 5,586,550; 5,758,637 and 6,085,740, the complete disclosures of which are herein incorporated by reference.

When vibrating such vibratable members at ultrasonic frequencies, there is a need to ensure that a maximum amount of the vibrational energy is transferred from the piezoelectric transducer to the vibratable member, rather than to some surrounding structure. Otherwise, performance losses or performance variations may occur because of the forces that are transmitted through the material which couples the aerosol generator to surrounding structures, such as the housing of an aerosolization device.

Hence, this invention is related to ways to maximize the amount of vibrational energy transferred to the vibratable member, thereby maximizing the efficiency of the aerosol generator. In this way, the repeatability and performance of the aerosol generator are enhanced, irrespective of the devices into which the aerosol generators are integrated.

SUMMARY OF THE INVENTION

The invention provides for the vibrational isolation of an aerosol generator from surrounding structures. In one embodiment, this is accomplished by the design of an aerosol generator that comprises a vibratable member having a front, a rear, an outer periphery and a plurality of apertures extending between the front and the rear. A support element is disposed about the outer periphery of the vibratable member. A vibratable element is coupled to the support element and is configured to vibrate the vibratable member at ultrasonic frequencies. An isolating structure is coupled to the support element and is configured to couple the aerosol generator to a support structure, such as the housing of an aerosolization device. The isolating structure has a vibrational mechanical impedance that is sufficient to substantially vibrationally isolate the aerosol generator from the support structure. In this way, the aerosol generator may be operated at increased efficiencies and in a repeatable manner when coupled to surrounding structures.

Conveniently, the isolating structure and the support element may be integrated into a single component, thereby facilitating its manufacture. In one aspect, the isolating structure may comprise a plurality of arms that extend from the support element. These arms may have a wide variety of shapes and contours. For example, the arms may be bent, crimped, curved, or the like to facilitate vibrational isolation.

In another aspect, the isolating structure may comprise one or more elastomeric or plastic members. For example, the isolating structure may be constructed of an elastomeric or plastic washer. Conveniently, the washer may be coupled to the support element by forming tabs in the support element and inserting the washer between the tabs. As another example, the isolating structure may be constructed of a plurality of discrete elastomeric members or bellows that extend from the support element.

To facilitate vibrational isolation, the isolating structure may be configured so that it has a resonant frequency that is outside the operating range of the aerosol generator. Such an operating range for the aerosol generator may be about 50 kHz to about 250 kHz.

In a further aspect, the vibratable member may be dome shaped and include tapered apertures. Examples of such vibratable members are described in U.S. Pat. Nos. 5,586,550, 5,758,637 and 6,085,740, previously incorporated by reference.

The invention further provides an exemplary method for aerosolizing liquids. Such a method utilizes an aerosol generator having a vibratable member with apertures and a vibratable element to vibrate the vibratable member. According to the method, liquid is supplied to the vibratable member and the vibratable element is used to vibrate the vibratable member at an ultrasonic frequency to eject liquid droplets through the apertures. During vibration, an isolating structure is used to substantially vibrationally isolate the aerosol generator to enhance the operating performance of the aerosol generator. Further, the vibratable member may be vibrated at a frequency that is different from a fundamental frequency of the isolating structure to enhance the efficiency of the aerosol generator. As previously mentioned, a variety of isolating structures may be used to vibrationally isolate the aerosol generator from any surrounding structures. Such isolating structures also have resonant frequencies outside of the operating range of the aerosol generator.

In a further embodiment, the invention provides a method for forming an aerosol generator. According to the method, an isolating structure is stamped or coined out of a sheet of material. A vibratable member having a plurality of apertures is coupled to the isolating structure, and a vibratable element, such as a piezoelectric transducer, is coupled to the isolating structure or the vibratable member. The vibratable element is used to vibrate the vibratable member at ultrasonic frequencies while the isolating structure is used to vibrationally isolate the aerosol generator from surrounding structures. By forming the isolating structure in this way, the cost of producing the aerosol generator may be greatly reduced and the aerosol generator may be produced in higher volumes.

In one aspect, the isolating structure comprises an annular member and a plurality of arms extending from the annular member. In another aspect, the arms are bent or crimped after the isolating structure has been stamped. In a further aspect, the vibratable member is coupled across a central opening of the annular member, and the vibratable element comprises an annular piezoelectric element that is coupled to the annular member.

Another method for forming an aerosol generator uses a support element having an outer periphery. A plurality of tabs are formed in the outer periphery of the support element. This may be accomplished by making a pair of cuts in the support element and then bending the material between the cuts away from the support element. A vibratable member having a plurality of apertures is coupled to the support element, and a vibratable element is coupled to the support element or the vibratable member and is vibratable at ultrasonic frequencies. A gasket is coupled about the support element, with the gasket being received into the tabs. The gasket has a mechanical vibrational impedance that is sufficient to substantially vibrationally isolate the aerosol generator. Such a process is useful in producing an isolated aerosol generator in a time and cost efficient manner.

BRIEF DESCRIPTION OF THE DRAWINGS

FIG. 9 is cross sectional view of another embodiment of an aerosol generator according to the invention.

FIG. 10 is a perspective view of a support element and an isolating structure of the aerosol generator of FIG. 9.

FIG. 11 is a perspective view of the support element of FIG. 10 prior to the formation of tabs that are employed to hold the isolating structure.

DESCRIPTION OF THE SPECIFIC EMBODIMENTS

Figure 1:
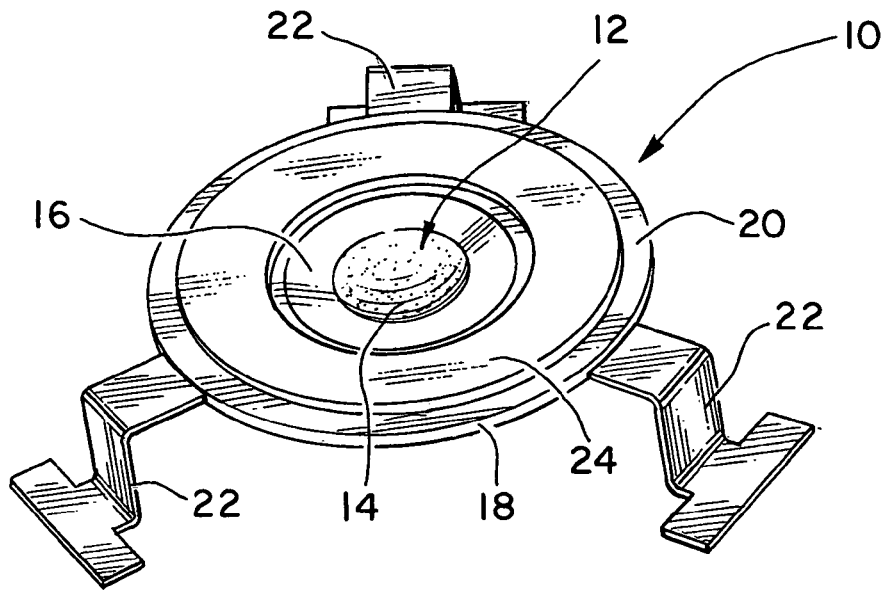
FIG. 1 is a rear perspective view of one embodiment of an aerosol generator according to the invention.

The invention provides techniques and devices to vibrationally isolate an aerosol generator from surrounding structures to which the aerosol generator is coupled. In some cases, the surrounding structures will be the housing of an aerosolizer or nebulizer, or various structures within such devices. Such aerosolization or nebulization devices can have complex geometry's as well as complicated fluid delivery and packaging requirements that can affect the operation of the aerosol generator.

The aerosol generators of the invention may comprise a vibratable member having a plurality of apertures, such as an aperture plate, through which liquid droplets are ejected and a piezo electric transducer to vibrate the aperture plate. The transducer is configured to vibrate the aperture plate at ultrasonic frequencies, typically within the range from about 50 kHz to about 250 kHz. Non-limiting examples aerosol generators utilizing such components are described in U.S. Pat. Nos. 5,164,740; 5,938,117; 5,586,550; 5,758,637 and 6,085,740, incorporated herein by reference.

The aerosol generators of the invention utilize an isolation system that is designed to accommodate nearly all types of external interfaces to enhance the repeatability and performance of the aerosol generator. In this way, the aerosol generators may be placed into a wide variety of complex aerosolization or nebulization devices without significantly compromising their operation. The isolation systems have a mechanical vibrational impedance that prevents the force transmitted at the edge of the aerosol generator from reaching the surrounding structure. Such a phenomenon may be characterized as the transmissibility and is defined as the ratio of the force experienced by the surrounding structure to the force produced at the edge of the aerosol generator. According to the invention, the transmissibility is less than about 30%, more preferably less than about 20%, and most preferably less than about 10%. In some cases the transmissibility has been measured to be less than about 6% and at about 2% to 3% at resonance.

The isolation system may be constructed of either discrete or continuous elements and may have a wide variety of shapes and sizes. For example, the isolation system may be constructed of thin metals arms, elastomer bushings, plastic legs, elastomer edges, and the like. Types of materials that may be used to construct such elements include silicone, urethane, elastomers, thin or curved metals, and the like.

The isolating systems of the invention are also configured to have a resonant frequency that is outside of the operating frequency of the aerosol generator. In this way, the isolating structure does not resonate during operation of the aerosol generator, thereby enhancing the performance and repeatability of the aerosol generator.

Another feature of the invention is that the isolating systems may be incorporated into the aerosol generators in such a way that the aerosol generators may be fabricated in high volumes and at reasonable costs. This may be accomplished, for example, by utilizing an isolating structure to both vibrationally isolate the aerosol generator and to support the aperture plate. Such isolating structures may conveniently be formed by stamping, coining, molding, and the like.

Referring now to FIG. 1, one embodiment of an aerosol generator 10 having an isolating system will be described. Aerosol generator 10 comprises a vibratable member 12 having a front (hidden from view), a rear 14 and an outer periphery 16. Although not shown, vibratable member has a plurality of apertures that taper from rear 14 to the front. Examples of vibratable members that may be used with the invention are described generally in U.S. Pat. Nos. 5,164,740; 5,938,117; 5,586,550; 5,758,637 and 6,085,740, incorporated by reference. As shown, vibratable member 12 is dome shaped in geometry. However, it will be appreciated that other shapes and sizes of vibratable members may be used, and the invention is not intended to be limited to a specific type of vibratable member.

Vibratable member 12 is coupled to an isolating structure 18 that also functions as a support member to support vibratable member 12. Isolating structure comprises an annular body 20 and a set of arms 22 that are used to couple aerosol generator 10 to another structure, such as the housing of an aerosolization device. Annular body 20 is secured about outer periphery 16 of vibratable member 12 so that the center of vibratable member is free to eject liquid droplets. Coupled to annular body 20 is an annular piezo electric element 24 that is used to vibrate vibratable member 12 when current is supplied to piezo electric element 24.

In use, arms 22 are employed to prevent the transmission of forces at the outer edge of body 20 from reaching surrounding structures so that aerosol generator 10 is substantially vibrationally isolated from any surrounded structures to which arms 22 may be coupled. In this example, arms 22 may be constructed of aluminum, steel, elastomers, plastic and the like and may have one or more bends to facilitate mounting of aerosol generator 10 to another structure and to prevent force transmission. Further, although shown with three arms, aerosol generator 10 may be constructed to have different numbers of arms, such a two, four, five, or the like. With such a construction, aerosol generator 10 may be operated in a repeatable manner, i.e., the aerosol generator is able to consistently produce droplets within a given size range and within a given range of flow rates. Further, this embodiment has shown to have a transmissibility at about 2% at resonance.

Figure 2:
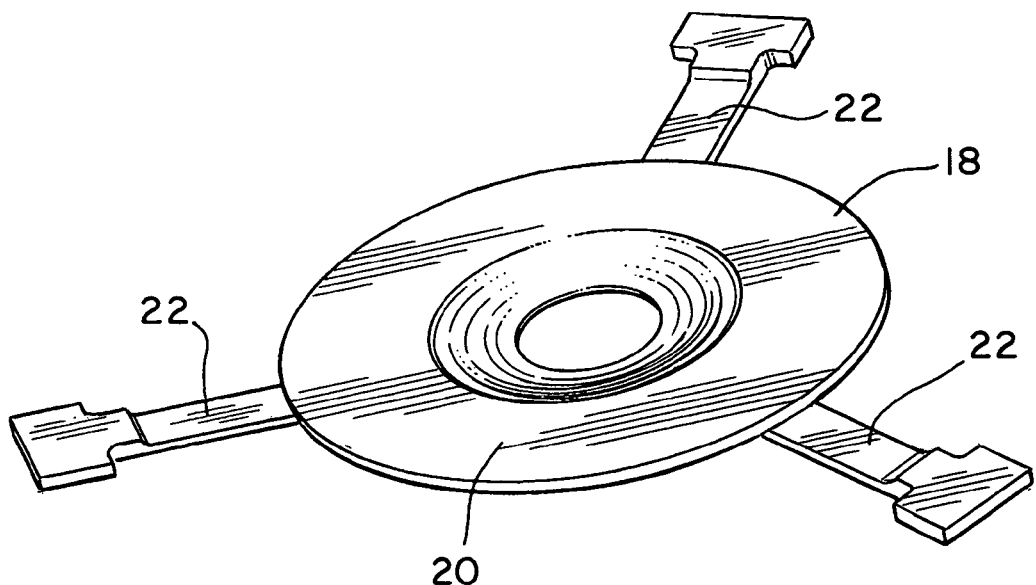
FIG. 2 is a rear perspective view of an isolating structure of the aerosol generator of FIG. 1 prior to assembly of the aerosol generator.

As shown in FIG. 2, isolating structure 18 may be stamped from a sheet of material. Once stamped, vibratable member 14 and piezo electric element 24 may be bonded to body 22. Arms 22 may also be bent to the desired shape. Such a process lends itself to high volume production at reasonable costs.

Figure 3:
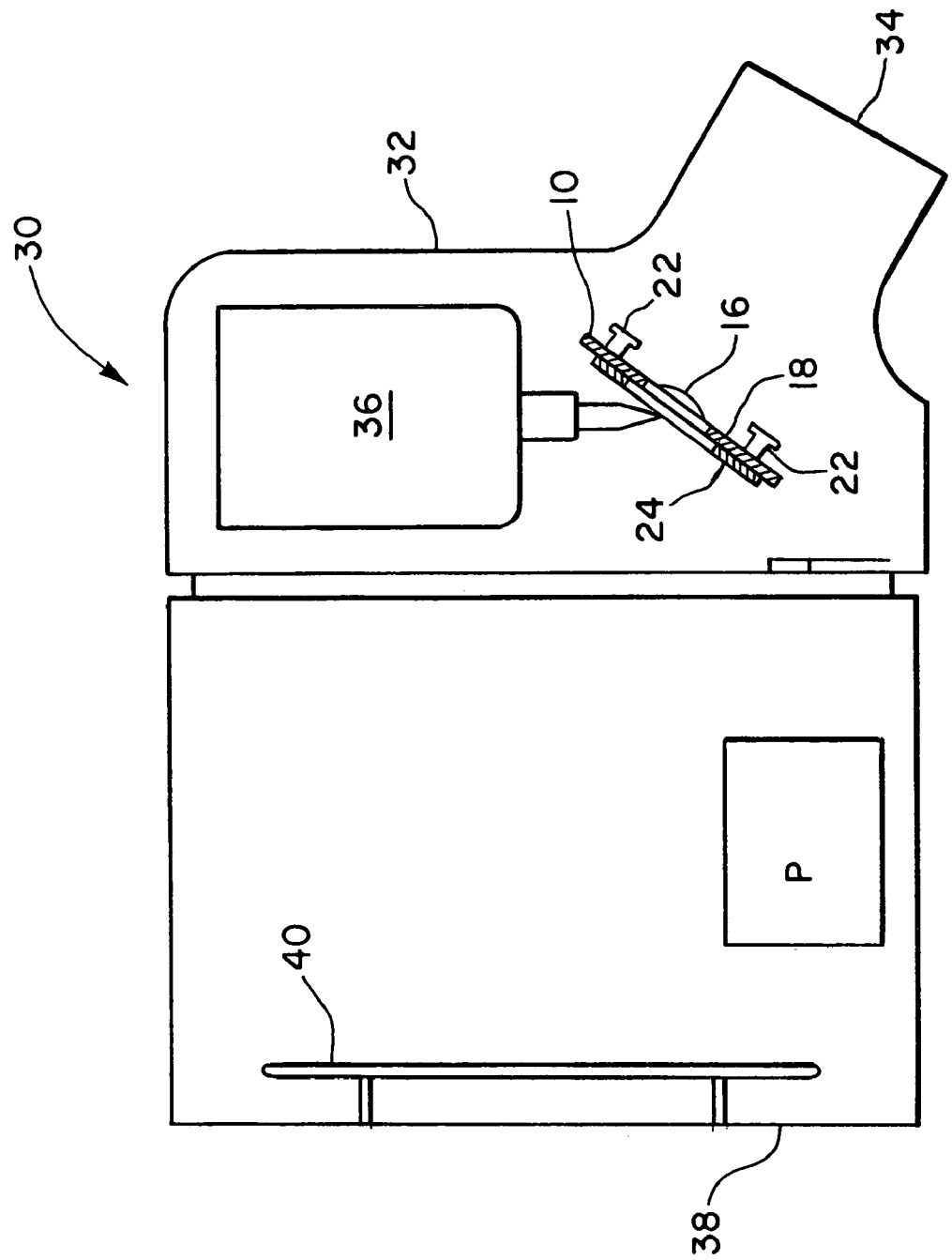
FIG. 3 illustrates an aerosolization device having the aerosol generator of FIG. 1.

Referring now to FIG. 3, aerosol generator 10 is shown coupled to an aerosolization device 30. Device 30 comprises a housing 32 to hold the various components of aerosolization device 30. Housing 32 further includes a mouthpiece 34 and one or more vents (not shown) to permit air to enter into housing 32 when a user inhales from mouthpiece 34. Disposed within housing 32 is aerosol generator 10 of FIG. 1. However, it will be appreciated that any of the aerosol generators described herein may be placed into housing 32. Aerosol generator 10 is coupled to housing 32 by arms 22 that also serve as an isolating structure to vibrationally isolate aerosol generator 10 from housing 32 in a manner similar to that described herein.

Aerosolization device 30 further includes a canister 36 having a supply of liquid that is to be aerosolized by aerosol generator 10. Canister 36 may include a metering valve to place a metered amount of liquid onto aperture plate 16. Although not shown, a button or the like may be employed to dispense the volume of liquid when requested by the user.

Housing 32 includes an electronics region 38 for holding the various electrical components of aerosolization device 30. For example, region 38 may include a printed circuit board 40 which serves as a controller to control operation of the aerosol generator 10. More specifically, circuit board 40 may send (via circuitry not shown) an electrical signal to the piezoelectric element 24 to cause aperture plate 16 to be vibrated. A power supply P, such as one or more batteries, is electrically coupled to circuit board 40 to provide aerosolization device 30 with power.

Figure 4:
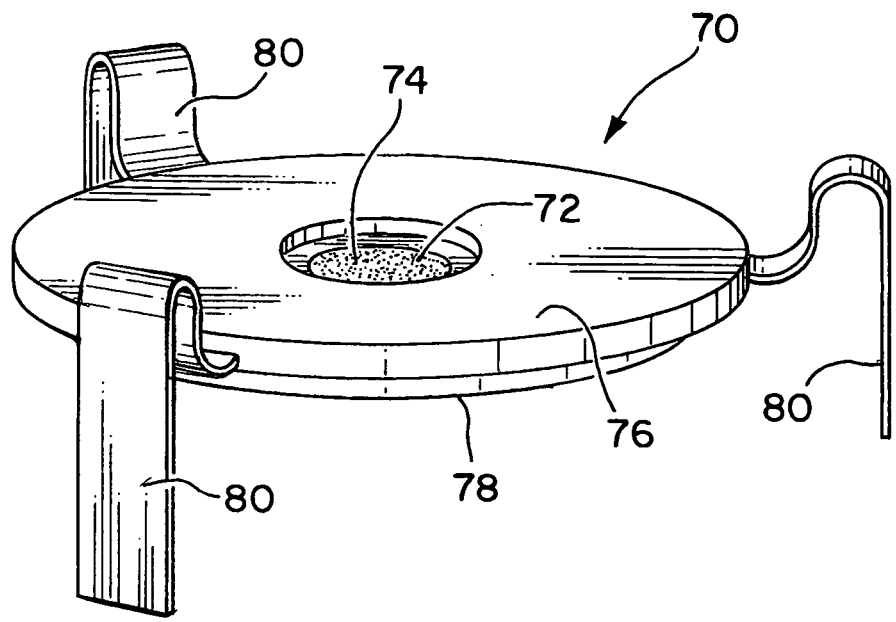
FIG. 4 is a front perspective view of another embodiment of an aerosol generator according to the invention.

FIG. 4 illustrates an alternative embodiment of an aerosol generator 70. Aerosol generator 70 comprises a vibratable member 72 having a front 74, a rear (not shown) and a plurality of apertures. Vibratable member 72 is coupled to a support member 76 that also supports a piezo electric element 78. Extending from support member 76 are a set of curved arms 80 that function as an isolating structure to vibrationally isolate aerosol generator from other structures to which arms 80 are coupled. Arms 80 may be constructed materials similar to those described in connection with FIG. 1. Further, although shown with only one curve, in some cases each arm may include multiple curves or bends to facilitate vibrational isolation of aerosol generator 70.

Figure 5:
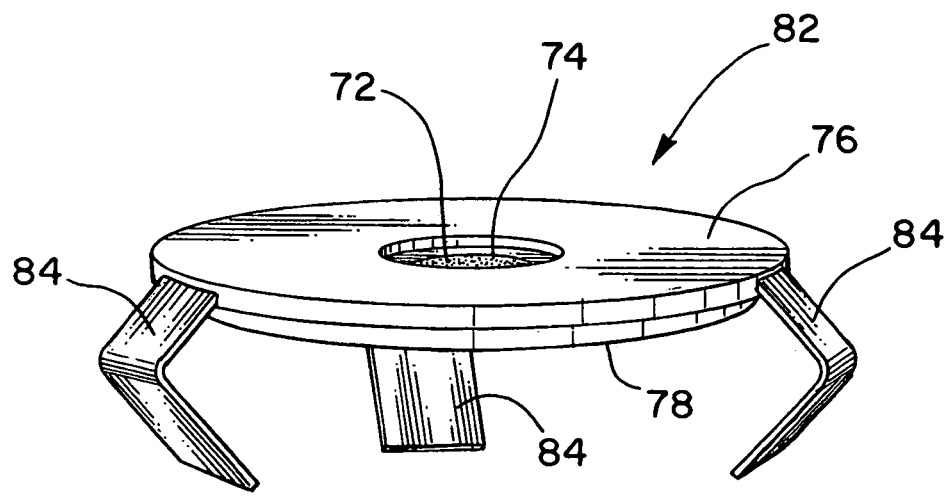
FIG. 5 is a side perspective view of a further embodiment of an aerosol generator according to the invention.

FIG. 5 illustrates another embodiment of an aerosol generator 82 having an alternative isolation system. Aerosol generator 82 is similar to aerosol generator 70 except for the configuration of the arms. For convenience of discussion, similar elements will be referred to with the same reference numerals used in FIG. 4. Aerosol generator 82 utilizes a set of angled arms 84 that are connected to support member 76. Although shown with one angled bend, arms 84 may alternatively have multiple angled bends, that may or may not have the same angle of bend.

Figure 6:
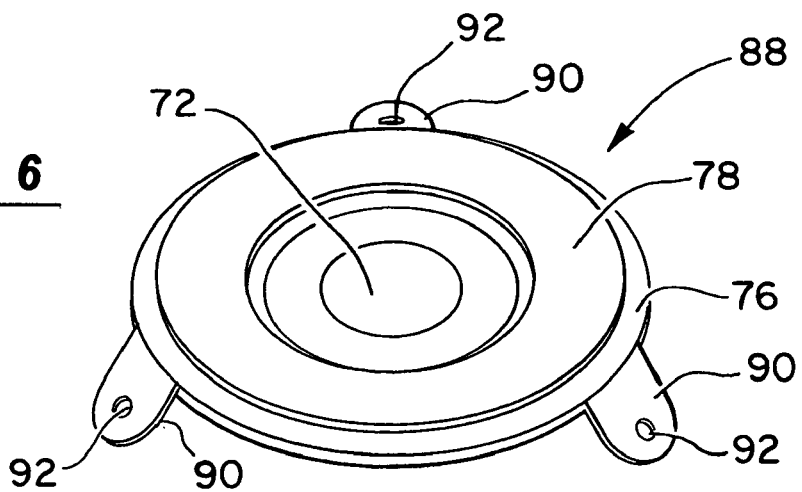
FIG. 6 is a rear perspective view of yet another embodiment of an aerosol generator according to the invention.
Figure 7:
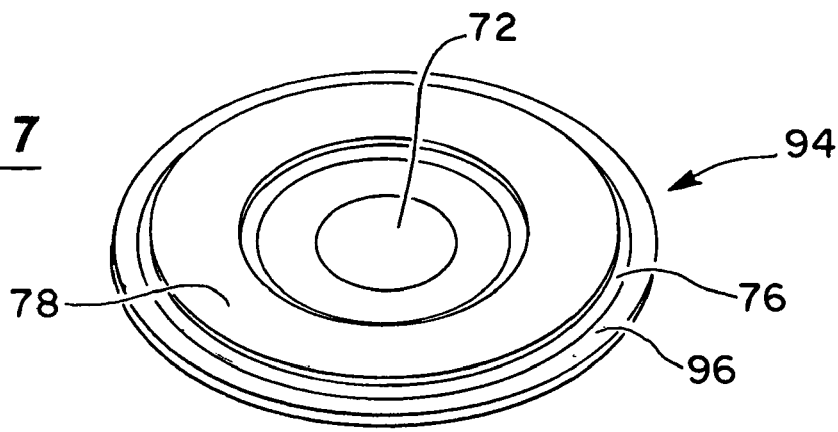
FIG. 7 is a rear perspective view of still another embodiment of an aerosol generator according to the invention.
Figure 8:
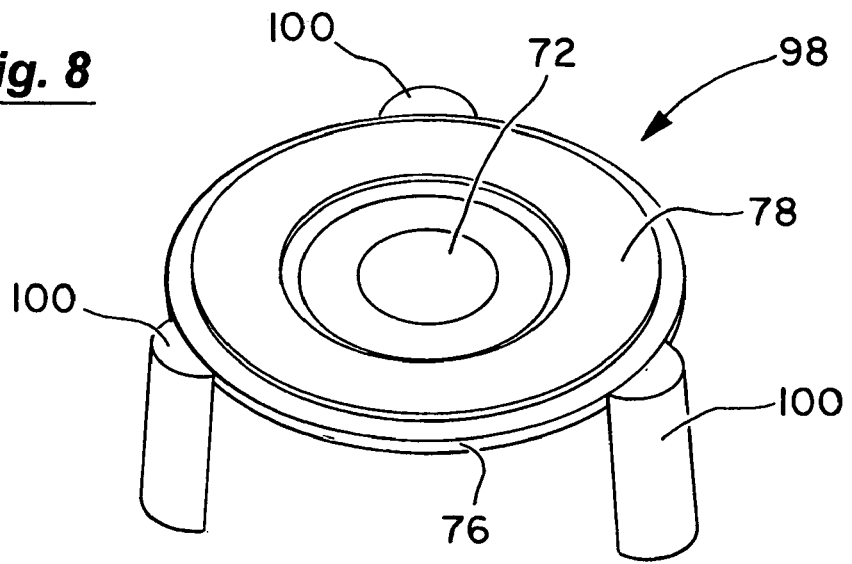
FIG. 8 is a rear perspective view of one particular embodiment of an aerosol generator according to the invention.

FIGS. 6–8 illustrate further alternative embodiments of aerosol generators having different isolation systems. These aerosol generators are similar to aerosol generator 70 except for the isolating structure. For convenience of discussion, similar elements will be referred to with the same reference numerals used in FIG. 4. FIG. 6 illustrates an aerosol generator 88 having a set of tabs 90 that are connected to support member 76 and are used to vibrationally isolate aerosol generator 88 from surrounding structures to which tabs 90 are connected. Tabs 90 may be constructed of materials such as those described with previous embodiments, and may be more or less in number than shown in the drawing. Tabs 90 may optionally include mounting holes 92 to facilitate mounting of the tabs to another structure. In some cases, tabs 90 and support structure 76 may be formed together in an insert molding process as described generally in copending U.S. patent application Ser. No. 09/848,111, filed on the same date as the present application, incorporated herein by reference.

FIG. 7 illustrates an aerosol generator 94 having an elastomeric ring 96 that is coupled about the outer periphery of support member 76. Elastomeric ring 96 serves as an isolating structure to vibrationally isolate aerosol generator 94 from surrounding structures to which ring 96 may be coupled. Alternatively, a plastic material may be used to form ring 96.

FIG. 8 illustrates an aerosol generator 98 having a set of discrete elastomeric elements 100 that are disposed about the outer periphery of support member 76. These elements may be constructed of elastomeric or plastic materials similar to those described in FIG. 7 and may be more or less in number than three. Elements 100 are employed to vibrationally isolate aerosol generator 98 from surrounding structures to which elements 100 are connected.

Shown in FIG. 9 is a cross sectional view of an aerosol generator 110 having an isolation system and which may be manufactured in a time and cost efficient manner. Aerosol generator 110 is constructed of a support element 112 that is used to hold a vibratable member 114 having a plurality of apertures in a manner similar to that described with other embodiments. As also shown in FIG. 10, support element 112 has a central aperture 116 across which vibratable member 114 is positioned and a circular outer periphery 118. Coupled to support element 112 is a vibratable element 120 to vibrate vibratable member 114 when aerosolizing a liquid.

Support element 112 may be manufactured by stamping support element 112 from a sheet as material such that is it in the shape of a disc or washer. As shown in FIG. 11, pair of cuts 122 and 124 are formed in support element 112 at the outer periphery 118 to form a set of tabs 126. Tabs 126 are then pressed or bent away from support element 112 to form a slot between tabs 126 and support element 112 as shown in FIG. 9. An isolating member 128 may then be inserted about outer periphery 118 by inserting isolating member 128 between tabs 126. Conveniently, isolating member 128 may comprise a resilient gasket that may be slipped between tabs 126. As with other embodiments, isolating member 128 may be used to vibrationally isolate the aerosol generator from surrounding structures.

The invention has now been described in detail for purposes of clarity of understanding. However, it will be appreciated that certain changes an modifications may be practiced within the scope of the appended claims.

What is claimed is:

1. An aerosol generator system comprising:
   an aerosol generator comprising a vibratable member having a front, a rear and a plurality of apertures extending between the front and the rear, wherein the aerosol generator is configured to produce liquid droplets when operated at a certain vibrational frequency;

an isolating structure operably coupled to the aerosol generator and that is configured to couple the aerosol generator to a support structure, wherein the isolating structure has a vibrational impedance that is sufficient to substantially vibrationally isolate the aerosol generator from the support structure, and wherein the isolating structure comprises a plurality of arms extending from the aerosol generator.

2. An aerosol generator system as in claim 1, wherein the plurality of arms extended from a support element disposed about an outer periphery of the vibratable member; and a vibratable element coupled to the support element, the vibratable element being configured to vibrate the vibratable member at ultrasonic frequencies, and wherein the isolating structure and the support element are integrally formed together.

3. An aerosol generator system as in claim 2, wherein the isolating structure is configured such that the ratio of forces transmitted to the support structure to forces at an outer edge of the support element is less than about 30%.

4. An aerosol generator system as in claim 3, wherein the ratio is less than about 20%.

5. An aerosol generator system as in claim 2, wherein the isolating structure has resonant frequencies that are outside of an operating frequency range of the aerosol generator.

6. An aerosol generator system as in claim 5, wherein the operating frequency range is about 50 kHz to about 250 kHz.

7. An aerosol generator system as in claim 1, wherein the arms have a contoured shape.

8. An aerosol generator system as in claim 1, wherein the vibratable member has a center portion containing the apertures, wherein the center portion is dome shaped in geometry, and wherein the apertures taper from the rear to the front.

9. An aerosolization device comprising:
a housing; and
an aerosol generator disposed within the housing, the aerosol generator comprising a vibratable member having a front, a rear and a plurality of apertures extending between the front and the rear, wherein the vibratable member is configured to vibrate at ultrasonic frequencies, an isolating structure coupled to the aerosol generator, and operably connected to the housing, wherein the isolating structure has a vibrational impedance that is sufficient to substantially vibrationally isolate the aerosol generator from the housing; and
wherein the isolating structure comprises a plurality of arms extending from the aerosol generator.

10. A device as in claim 9, wherein the plurality of arms extended from a support element disposed about an outer periphery of the vibratable member, a vibratable element coupled to the support element to vibrate the vibratable member, wherein the isolating structure and the support element are integrally formed together.

11. A device as in claim 10, wherein the isolating member is configured such that the ratio of forces transmitted to the support element to forces at an outer edge of the support element is less than about 30%.

12. A device as in claim 11, wherein the ratio is less than about 10%.

13. A device as in claim 9, wherein the arms have a contoured shape.

14. A device as in claim 9, wherein the isolating structure has resonant frequencies that are outside of an operating frequency range of the aerosol generator.

15. A device as in claim 14, wherein the operating frequency range is about 50 kHz to about 250 kHz.

16. A device as in claim 9, wherein the vibratable member has a center portion containing the apertures, wherein the center portion is dome shaped in geometry, and wherein the apertures taper from the rear to the front.

17. A method for aerosolizing a liquid, the method comprising:
providing an aerosol generator comprising a vibratable member having a front, a rear, and a plurality of apertures extending between the front and the rear, and a vibratable element to vibrate the vibratable member;
supplying a liquid to the rear of the vibratable member; and
vibrating the vibratable member with the vibratable element to eject liquid droplets through the apertures while substantially vibrationally isolating the aerosol generator with an isolating structure that is operably coupled to a support structure;
wherein the isolating structure comprises a plurality of arms extending from the aerosol generator, wherein the isolating structure is configured to vibrationally isolate the aerosol generator from the support structure.

18. A method as in claim 17, further comprising vibrating the vibratable member at a frequency that is different than a resonant frequency of the isolating structure, and wherein the vibratable member is vibrated at a frequency in the range from about 50 kHz to about 250 kHz, and wherein the ratio of forces transmitted to the support structure to forces at an outer edge of the aerosol generator is less than about 30%.

* * * * *